United States Patent [19]
Rosenberg

[11] Patent Number: 5,100,395
[45] Date of Patent: Mar. 31, 1992

[54] FLUID DRAIN FOR WOUNDS

[76] Inventor: Lior Rosenberg, 13 Harduf Street, Omer, Beer, Sheba, Israel

[21] Appl. No.: 594,799

[22] Filed: Oct. 9, 1990

[30] Foreign Application Priority Data

Oct. 6, 1989 [IL] Israel .................................. 91918

[51] Int. Cl.⁵ ............................................. A61M 25/00
[52] U.S. Cl. ..................................... 604/284; 604/247
[58] Field of Search .............. 604/128, 129, 264, 268, 604/275, 284, 282, 283, 180, 174, 247, 256, 43, 45, 280, 247, 31, 237; 128/DIG. 26

[56] References Cited

U.S. PATENT DOCUMENTS

| | | | |
|---|---|---|---|
| 340,739 | 4/1886 | Stohlmann | 92/92 |
| 4,072,153 | 2/1978 | Swartz | 604/284 |
| 4,227,533 | 10/1980 | Godfrey | 604/247 |
| 4,257,422 | 3/1981 | Duncan | 604/282 |
| 4,573,965 | 3/1986 | Russo | 604/43 |
| 4,579,120 | 4/1986 | MacGregor | 604/180 |
| 4,579,555 | 4/1986 | Russo | 604/282 |
| 4,838,881 | 6/1989 | Bennett | 604/283 |
| 4,919,167 | 4/1990 | Manska | 604/247 |
| 4,925,452 | 5/1990 | Melinyshyn et al. | 604/284 |

FOREIGN PATENT DOCUMENTS

| | | | |
|---|---|---|---|
| 0333308 | 9/1989 | European Pat. Off. | 604/284 |
| 0358536 | 9/1922 | Fed. Rep. of Germany | 604/174 |
| 1285953 | 1/1962 | France | 604/43 |
| 0502188 | 3/1939 | United Kingdom | 604/247 |

*Primary Examiner*—C. Fred Rosenbaum
*Assistant Examiner*—Sharon Finkel
*Attorney, Agent, or Firm*—Benjamin J. Barish

[57] ABSTRACT

A fluid drain for wounds includes a tube having one end insertable under the patient's skin into the wound, with the opposite end of the tube extending externally of the patient's skin; and a valve assembly at the opposite end of the tube. The valve assembly includes a first port for connection to a vacuum source, a second port connected to the opposite end of the tube, a third port for outletting the drained fluid into a container, a first one-way valve permitting the fluid to flow freely therethrough only from the second port to the first port, and a second one-way valve permitting the fluid to flow freely therethrough only from the first port to the third port.

20 Claims, 2 Drawing Sheets

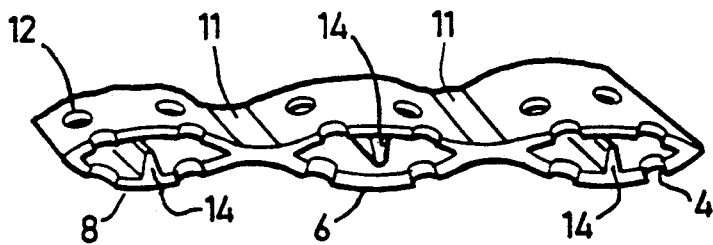
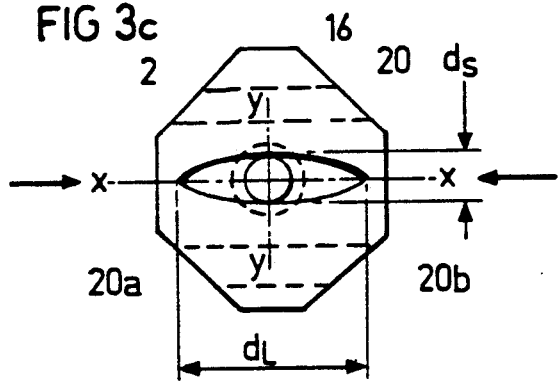
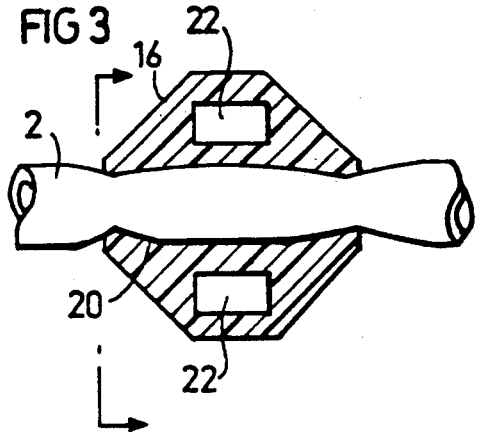
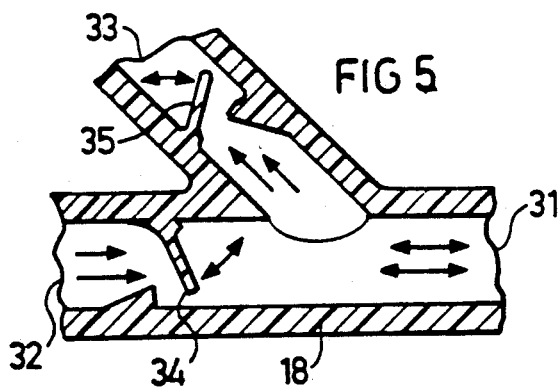
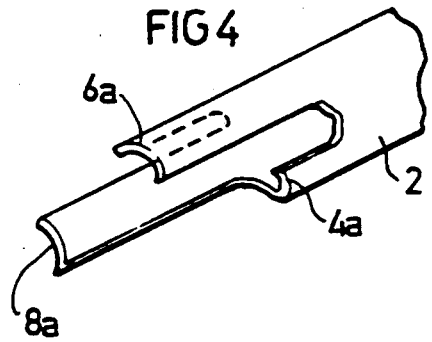
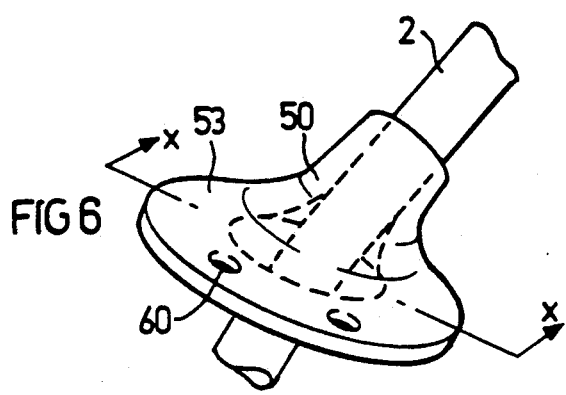
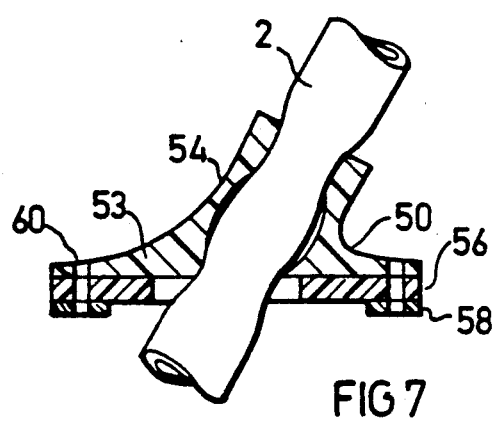

FLUID DRAIN FOR WOUNDS

FIELD AND BACKGROUND OF THE INVENTION

The present invention relates to fluid drains for wounds such as are used for promoting healing of the wounds.

Accumulation of fluid in a closed operation field is one of the commonest surgical complications. If this fluid becomes infected, the situation may become very critical. The fluid may be evacuated by using a "passive" technique, in which only gravitational, capillary, or surface tension forces are used to move the collected fluids from the wounds, usually into the dressing. A more effective way of draining the fluid is by an "active" technique, in which a vacuum source is provided to draw the fluid under a predetermined force from the wound into a hermetically closed container. Once the vacuum is applied, the container, drain and wound form a closed system with the liquid flowing in one direction only, namely to the container.

By definition, a "fluid drain" in an active system is the tube which connects a body cavity or wound with the vacuum source and/or container.

After the fluid has entered the drain, the fluid is deprived of the protective immune mechanisms of the body, as well as of the benefit of any administered drug. Accordingly, there is nothing to prevent the bacteria from multiplying in the fluid, which acts as an "in vitro" culture. For this reason, fluid in the drain and in the container should be considered contaminated and should not be allowed to reflux into the wound.

OBJECTS AND BRIEF SUMMARY OF THE INVENTION

An object of the present invention is to provide an improved fluid drain for application to a wound in order to promote healing.

According to one aspect of the present invention, there is provided a fluid drain for wounds, comprising: a tube having a subcutaneous tubelet at one end insertable under the patient's skin into the wound, with the opposite end of the tube extending externally of the patient's skin; an anchoring member for anchoring the one end of the tube to the patient's skin; and a valve assembly at the opposite end of the tube; said valve assembly comprising: a first port for connection to a vacuum source; a second port connected to said opposite end of the tube; a third port for outletting the drained fluid into a container; a first one-way valve permitting the fluid to flow freely therethrough only from the second port to said first port; and a second one-way valve permitting the fluid to flow freely therethrough only from the first port to the third port.

In the preferred embodiment of the invention described below, each of the one-way valves is a flap-type valve.

According to another important feature in the preferred embodiment of the invention described below, the one end of the tube includes at least two subcutaneous tubelets, enabling the device to be used as a simple drain having an extended area coverage.

In the described preferred embodiment, each of the subcutaneous tubelets includes an inner protrusion to prevent collapse; also, the tubelets are integrally formed on a sleeve applied to one end of the tube, and that end of the tube is formed with cut-outs which terminate at different axial locations of the tube, such that the tubelets nest sequentially within the tube when the tubelets are withdrawn from under the patient's skin. In the described preferred embodiment, the fluid drain terminates in three subcutaneous tubelets.

According to another feature in the described preferred embodiment, the anchoring member is of soft, resilient material and has an opening therethrough for receiving the tube, the opening being of generally elliptical cross-section having a length along its minor axis smaller than the outer diameter of the tube so as to firmly grip the tube, and a length along its major axis larger than the outer diameter of the tube, such that squeezing the anchoring member along its major axis releases the tube and thereby enables the anchoring member to be moved to any desired location along its length.

Further features and advantages of the invention will be apparent from the description below.

BRIEF DESCRIPTION OF THE DRAWINGS

The invention is herein described, by way of example only, with reference to the accompanying drawings, wherein:

FIG. 2 is a sectional view along lines II—II of FIG. 1 illustrating the construction of the subcutaneous tubelets formed in one end of the fluid drain of FIG. 1 insertable under the patient's skin into the wound;

FIG. 3 is a sectional view illustrating the construction of the anchoring member in the fluid drain of FIG. 1;

FIG. 3a is a sectional view along lines a—a of FIG. 3;

FIG. 4 is a fragmentary view illustrating the end of the drain tube receiving the tubelets;

FIG. 5 is a sectional view illustrating the construction of the valve assembly for connecting the opposite end of the fluid drain to the vacuum source;

FIG. 6 illustrates another construction of anchoring member that may be used;

and FIG. 7 is a sectional view illustrating the construction of the anchoring member of FIG. 6.

DESCRIPTION OF PREFERRED EMBODIMENTS

Figure 1:
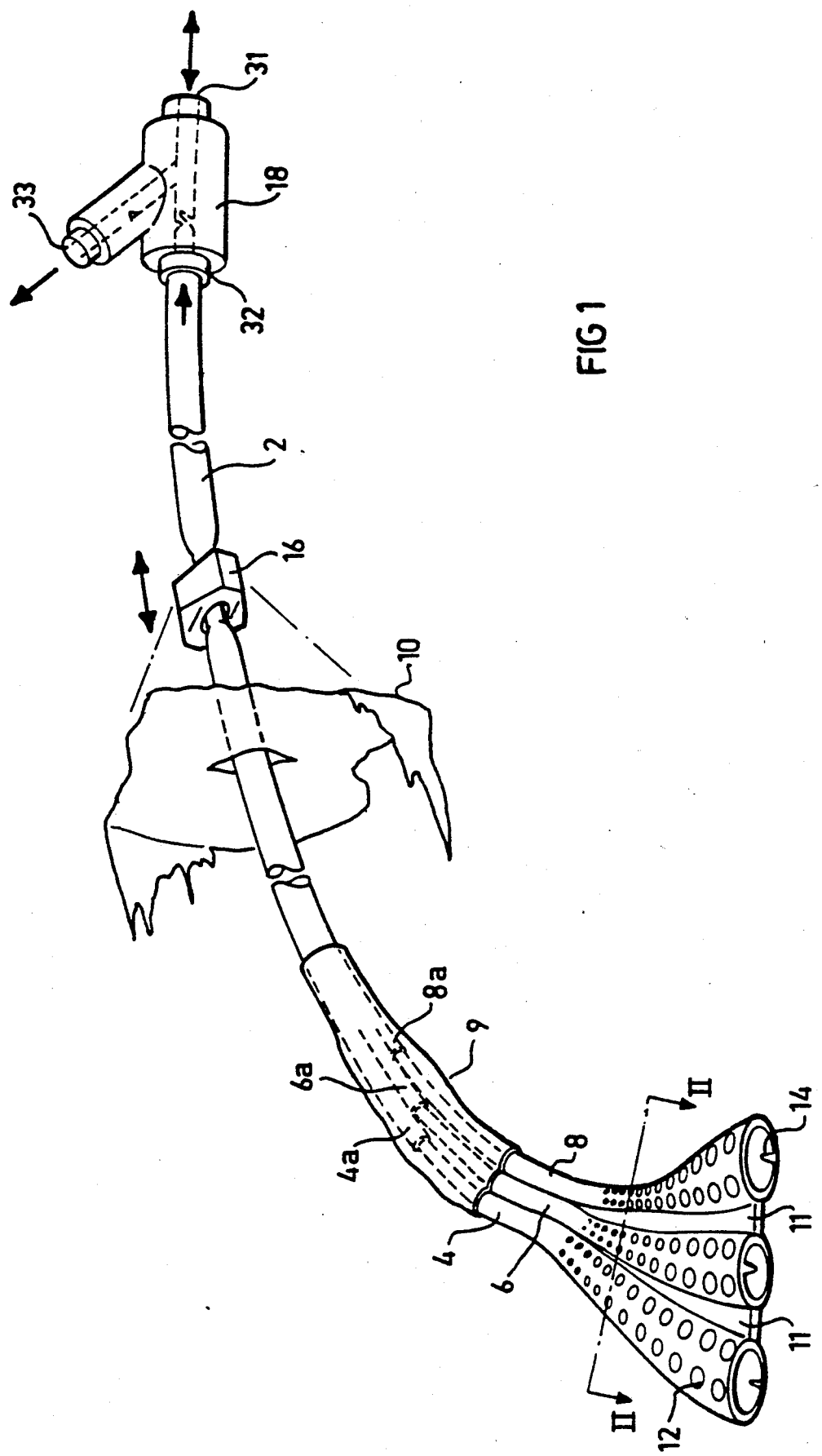
FIG. 1 illustrates one form of fluid drain constructed in accordance with the present invention.

The fluid drain illustrated in FIG. 1 of the drawings comprises a tube 2 having one end (left end in FIG. 1) insertable under the patient's skin into the wound, and the opposite end (right end in FIG. 1) extending externally of the skin for connection to a vacuum source (not shown), such as a syringe, a suction pump, or a bellows.

The end of tube 2, (left end, FIG. 1) insertable under the patient's skin terminates in three (or more) subcutaneous tubelets, shown at 4, 6, and 8 respectively. These subcutaneous tubelets are integrally formed on a sleeve 9 which is fixed, e.g., by adhesive, to the respective end of tube 2. That end of tube 2 together with sleeve 9 and its tubelets 4, 6, 8, are to be inserted under the patient's skin into the wound (the skin line being shown at 10), whereas the remainder of tube 2 is intended to extend externally of the patient's skin.

The subcutaneous tubelets 4, 6, 8 are connected together by webs 11 so as to be exposed to a relatively large surface area when inserted under the patient's skin. The tubelets are of oblong, i.e., a lenticular or "lens-shaped" cross-section, and are not of rectangular cross-section as is known in the art, so as to minimize the protrusions pressing against the surrounding tissue. Each of the subcutaneous tubelets 4, 6, 8 is formed with a plurality of perforations or openings 12 through the tubelet wall to provide a large surface area for the fluids to enter, and each tubelet is further formed with an internal web or projection 14 extending longitudinally of its length to prevent collapse of the tubelet when inserted under the patient's skin.

The portion of the drain tube 2 which is to be disposed externally of the patient's skin (i.e., the portion to the right of skin line 10, FIG. 1) includes an anchoring member 16 for anchoring the drain tube to the patient's skin, and also a valve housing 18 for connecting the end of the drain tube to the vacuum source.

The construction of anchoring member 16 is more particularly illustrated in FIGS. 3 and 3a. It is made of soft, resilient material, such as natural or synthetic rubber, and is formed with an opening 20 therethrough for receiving the drain tube 2.

As shown particularly in FIG. 3a, opening 20 through the anchoring member 16 is of oblong or elliptical cross-section, having a length $d_s$ along its minor axis y—y which is smaller than the outer diameter of the drain tube 2, and a length $d_L$ along its major axis x—x which is larger than the outer diameter of the drain tube. Thus, in the normal condition of anchoring member 16, it firmly grips the drain tube 2, but if the anchoring member is squeezed along its major axis, as shown by the arrows in FIG. 3a, the length $d_s$ along its minor axis increases so as to release the drain tube 2. The anchoring member may then be moved along the drain tube to any desired location thereon, whereupon release of the anchoring member causes it to resume to its normal condition illustrated in FIG. 3a firmly gripping the drain tube. The opposite ends of anchoring member 16 are provided with surfaces, as shown at 20a, 20b, against which the user may apply his fingers to squeeze the anchoring member and thereby to release it from the drain tube 2.

This construction of anchoring member 16 provides a number of important advantages. One important advantage is that the anchoring member 16 may be conveniently used for pinch-closing the drain tube 2 when the vacuum source is disconnected, this being done by merely bending the right end of the drain tube 2, between anchoring member 16 and the valve assembly 18, to cause the respective end of the anchoring member 16 to pinch-close the tube, thereby the reducing the danger of reflux of contaminated fluid from outside the wound into the wound. Another advantage is that the oblong or elliptical shaped opening 20 in the anchoring member 16 provides a firm grip of the drain tube 2 in the natural condition of the anchoring member, but permits the anchoring member to be moved along the length of the drain tube to any desired location by merely squeezing the anchoring member along the major axis x—x, FIG. 3a, namely along the axis of arrows, as described above.

Anchoring member 16 further includes eyelets or openings 22 adapted to receive sutures for attaching the anchoring member to the patient's skin.

As shown in FIG. 4, the end of the drain tube 2 receiving sleeve 9 of the tubelets 4, 6, 8 is formed with three cut-outs 4a, 6a, 8a, one for and aligned with each of the tubelets 4, 6, 8. These cut-outs terminate at different axial locations of the drain tube 2 such that the tubelets can be received in or nest within the drain tube 2 when the drain tube, including sleeve 9 and the tubelets, are withdrawn from under the patient's skin. Since these cut-outs 4a, 6a, 8a terminate at different axial locations of the tube, this nesting of the tubelet is effected sequentially during their withdrawal from the wound. This arrangement reduces pain and discomfort to the patient, and also the size of the opening required, when withdrawing the tubelets from under the skin.

Valve housing 18 is more particularly illustrated in FIG. 5. It includes three ports and two one-way valve as follows: a first port 31 for connection to the vacuum source (e.g., a syringe, vacuum pump or bellows); a second port 32 for connection to drain tube 2; a third port 33 for outletting the drain fluid, e.g., to a hermetic drain fluid container (not shown); a first one-way valve 34 permitting the fluid to flow freely therethrough only in the direction from port 32 to port 31 during the withdrawal of the fluid by the vacuum produced by the vacuum device, or by internal pressure of the collected fluids; and a second one-way valve 35 permitting the fluid to flow freely therethrough only in the direction from port 31 to port 33, e.g., to enable the fluid drained from the wound and accumulated in the vacuum device to be ejected to the hermetic drain-fluid container (not shown) connected to port 33.

One-way valve 34 opens at a low pressure as compared to one-way valve 35, which latter valve opens at a higher pressure. Thus, valve 34 will open under the lower pressure produced by the vacuum device, whereas valve 35 will open only under the higher pressure when ejecting the fluid accumulated in the vacuum device to the drain-fluid container.

The manner of using the drain illustrated in FIGS. 1-5 will be apparent from the above description. Thus, the drain is applied to the wound with the portion of tube 2 left of the skin line 10, including sleeve 9 and its subcutaneous tubelets 4, 6, 8 inserted under the patient's skin into the wound, whereas the portion of the tube 2 to the right of the skin line 10 is exposed externally of the patient's skin. The opposite end of tube 2 is connected to port 32 of valve assembly 18. Port 31 of the valve assembly is connected to the source of vacuum, and port 33 of the valve assembly is connected to a hermetic container for receiving the drained fluid. Finally, anchoring member 16 is moved to the desired location on tube 2, by squeezing the anchoring member along its major axis x—x as shown in FIG. 3a to release it from the tube; the anchoring member is released at the desired location on the tube, whereupon the anchoring member restores to its normal condition as illustrated in FIG. 3a firmly gripping the tube. The anchoring member may then be fixed to the patient's skin by passing sutures through its eyelets 22.

In order to effect the drainage of the wound, suction is then applied to port 31 of valve assembly 18. A minimal suction causes valve member 34 to open, so that the suction is applied to the subcutaneous tubelets 4, 6, 8 under the patient's skin to draw out fluids and to pass them via valve 34 into the suction device. Valve 35 in port 33 of the valve assembly 18, connected to the hermetic container for receiving the drain fluids, is held closed by the suction force applied to port 31.

Whenever it is desired to empty the suction device of the accumulated drained fluids, a positive pressure is applied to port 31, whereupon valve member 34 automatically closes to prevent the drained fluids from refluxing into the wound, and valve 35 is opened permitting the drained fluids to be ejected to the hermetic container.

If the suction device is removed, or the suction is otherwise terminated, valve 34, which is closed, prevents a reflux of the drained fluids. For extra safety, drain tube 2 may be conveniently pinched closed by merely moving laterally (e.g., lifting) the side of the tube rightwardly of the anchoring member 16, whereupon the end of opening 20 formed through the anchoring member pinches-closed the tube. This arrangement thereby substantially eliminates the danger of contamination of the wound by the drained fluid which had accumulated in the suction device connected to port 31 or in the container connected to port 33.

When the wound has healed sufficiently to remove the drain, this may easily be done by first removing the sutures from the anchoring member 16, and then pulling out tube 2 together with sleeve 9 secured to it and the subcutaneous tubelets 4, 6, 8. The removal of the tubelets is facilitated by their nesting in the cut-outs 4a, 6a, 8a (FIG. 4) formed in the end of tube 2 as described above, thereby reducing the size of the opening required, and the pain and discomfort to the patient.

FIGS. 6 and 7 illustrate another form of anchoring member, therein designated 50, which may be used instead of anchoring member 16 in FIGS. 1-4. Anchoring member 50 is formed with an enlarged base 53 for application to the skin, and with an opening 54 extending through its base for receiving the drain tube (2, FIG. 1). Opening 54 in anchoring member 50 of FIGS. 6 and 7 is also shaped to have an oval or elliptical cross-section as described above with respect to FIGS. 1-5 so as to firmly grip the drain tube in the normal condition of the anchoring member, but to release the drain tube, by squeezing its opposite ends along its major axis (as shown by arrows x—x in FIG. 6) to permit the anchoring member to be moved any desired location on the drain tube.

The enlarged base 53 of anchoring member 50 is covered by a dressing 56 which has a pressure sensitive type of adhesive layer 58 at its ends for adhesively attaching the anchoring member to the patient's skin. Base 50 is also formed with holes 60 for receiving sutures in order to more securely fix the anchoring member to the patient's skin.

While the invention has been described with respect to several preferred embodiments, it will be appreciated that many other variations, modifications and applications of the invention may be made.

What is claimed is:

1. A fluid drain for wounds, comprising: a tube having a subcutaneous tubelet at one end insertable under the patient's skin into the wound, with the opposite end of the tube extending externally of the patient's skin; an anchoring member for anchoring said one end of the tube to the patient's skin; and a valve assembly at the opposite end of the tube; said valve assembly comprising: a first port for connection to a vacuum source; a second port connected to said opposite end of the tube; a third port for outletting the drained fluid into a container; a first one-way valve permitting the fluid to flow freely therethrough only from said second port to said first port; and a second one-way valve permitting the fluid to flow freely therethrough only from said first port to said third port.

2. The fluid drain according to claim 1, wherein each of said one-way valves is a flap-type valve.

3. The fluid drain according to claim 1, wherein said one end of the tube includes at least two subcutaneous tubelets, enabling the device to be used as a simple drain having an extended area coverage.

4. The fluid drain according to claim 3, wherein each of said subcutaneous tubelets includes inner projection to prevent collapse.

5. The fluid drain according to claim 3, wherein each of said subcutaneous tubelets is of oblong shape in cross-section, and is formed with a plurality of perforations through the tubelet wall.

6. The fluid drain according to claim 3, wherein said tube terminates in at least three subcutaneous tubelets.

7. The fluid drain according to claim 3, wherein said subcutaneous tubelets are integrally formed on a sleeve applied to said one end of the tube.

8. The fluid drain according to claim 7, wherein said one end of the tube is formed with cut-outs, said sleeve being applied to the tube such that the tubelets are aligned with different ones of said cut-outs and thereby tend to nest within the tube upon being withdrawn from under the patient's skin.

9. The fluid drain according to claim 8, wherein said cut-outs terminate at different axial locations of the tube, such that the tubelets nest sequentially within the tube when the tubelets are withdrawn from under the patient's skin.

10. The fluid drain according to claim 1, wherein said anchoring member is of soft, resilient material and has an opening therethrough for receiving the tube, said opening being of generally elliptical cross-section having a length along its minor axis smaller than the outer diameter of the tube so as to firmly grip the tube, and a length along its major axis larger than the outer diameter of the tube, such that squeezing the anchoring member along its major axis releases the tube and thereby enables the anchoring member to be moved to any desired location along the length of the tube.

11. The fluid drain according to claim 10, wherein said anchoring member is formed with a suture-receiving portion for attaching the anchoring member to the patient's skin by sutures.

12. The fluid drain according to claim 10, wherein said anchoring member includes an enlarged surface area covered by a dressing for contact with the patient's skin, and an adhesive layer for adhesively attaching the anchoring member to the patient's skin.

13. The fluid drain according to claim 12, wherein said opening through the anchoring member passes through said enlarged surface area covered by the dressing.

14. A fluid drain for wounds, comprising:
a tube having a subcutaneous tubelet at one end insertable under the patient's skin into the wound, with the opposite end of the tube extending externally of the patient's skin;
a valve assembly at the opposite end of the tube; said valve assembly comprising: a first port for connection to a vacuum source; a second port connected to said opposite end of the tube; a third port for outletting the drained fluid into a container; a first one-way valve permitting the fluid to flow freely therethrough only from said second port to said first port; and a second one-way valve permitting the fluid to flow freely therethrough only from said first port to said third port;
and an anchoring member applied to an external part of the tube for anchoring the tube to the patient's skin, said anchoring member being of soft, resilient material and having an opening therethrough for receiving the tube, said opening being of generally elliptical cross-section having a length along its minor axis smaller than the outer diameter of the tube so as to firmly grip the tube, and a length along its major axis larger than the outer diameter of the tube, such that squeezing the anchoring member along its major axis releases the tube and thereby enables the anchoring member to be moved to any desired location along its length.

15. The fluid drain according to claim 14, wherein said one end of the tube includes at least two subcutaneous tubelets, enabling the device to be used as a simple drain having an extended area coverage.

16. The fluid drain according to claim 15, wherein each of said subcutaneous tubelets is of oblong shape in cross-section, and is formed with a plurality of perforations through the tubelet wall.

17. The fluid drain according to claim 15, wherein said subcutaneous tubelets are integrally formed on a sleeve applied to said one end of the tube.

18. The fluid drain according to claim 17, wherein said one end of the tube is formed with cut-outs, said sleeve being applied to the tube such that the tubelets are aligned with different ones of said cut-outs and thereby tend to nest within the tube upon being withdrawn from under the patient's skin.

19. The fluid drain according to claim 18, wherein said cut-outs terminate at different axial locations of the tube, such that the tubelets nest sequentially within the tube when the tubelets are withdrawn from under the patient's skin.

20. The fluid drain according to claim 14, wherein said anchoring member includes an enlarged surface area covered by a dressing for contact with the patient's skin, and an adhesive layer for adhesively attaching the anchoring member to the patient's skin.

* * * * *